(12) United States Patent
Guerin et al.

(10) Patent No.: US 7,217,297 B2
(45) Date of Patent: May 15, 2007

(54) COMPOSITION FOR DYEING KERATIN FIBERS COMPRISING A DEFINED DIHETEROYLARYLMETHANE DIRECT DYE OR A LEUCO PRECURSOR OF THIS DYE AND DYEING METHOD USING IT

(75) Inventors: Frédéric Guerin, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 58 days.

(21) Appl. No.: 10/746,501

(22) Filed: Dec. 29, 2003

(65) Prior Publication Data

US 2004/0187229 A1 Sep. 30, 2004

Related U.S. Application Data

(60) Provisional application No. 60/450,358, filed on Feb. 28, 2003.

(30) Foreign Application Priority Data

Dec. 30, 2002 (FR) .................................. 02 16845

(51) Int. Cl.
*A61K 7/13* (2006.01)

(52) U.S. Cl. ................ 8/405; 8/406; 8/407; 8/426; 8/568; 8/570; 8/573; 8/659; 546/165

(58) Field of Classification Search ........... 8/405, 8/406, 407, 426, 568, 570, 573, 659; 546/165
See application file for complete search history.

(56) References Cited

U.S. PATENT DOCUMENTS

| | | |
|---|---|---|
| 3,418,117 A | 12/1968 | Becker |
| 3,423,427 A | 1/1969 | Cescon et al. |
| 3,627,893 A | 12/1971 | Seeger |
| 3,652,556 A | 3/1972 | Kuhlthau et al. |
| 3,685,956 A | 8/1972 | Raue et al. |
| 3,995,088 A | 11/1976 | Garner et al. |
| 4,054,718 A | 10/1977 | Garner et al. |
| 4,154,463 A | 5/1979 | Burri |
| 4,254,032 A | 3/1981 | Petitpierre et al. |
| 4,340,540 A | 7/1982 | Hermann |
| 4,355,823 A | 10/1982 | Burri |
| 4,407,960 A | 10/1983 | Tratnyek |
| 4,460,385 A | 7/1984 | Pan et al. |
| 4,598,036 A | 7/1986 | Iwasaki et al. |
| 4,823,985 A | 4/1989 | Grollier et al. |
| 5,094,688 A * | 3/1992 | Eckstein et al. ............ 106/31.2 |
| 5,097,034 A * | 3/1992 | Eckstein .................... 546/165 |
| 5,266,699 A | 11/1993 | Naef et al. |
| 5,362,612 A | 11/1994 | Kiekens et al. |
| 5,708,151 A | 1/1998 | Mockli |
| 5,733,343 A | 3/1998 | Mockli |
| 5,888,252 A | 3/1999 | Mockli |

| | | |
|---|---|---|
| 2003/0066143 A1 | 4/2003 | Mockli |

FOREIGN PATENT DOCUMENTS

| | | |
|---|---|---|
| BE | 702 240 | 2/1968 |
| DE | 1 248 193 | 10/1964 |
| DE | 1 569 750 | 4/1967 |
| DE | 1 254 118 | 5/1968 |
| DE | 1 620 564 | 5/1970 |
| DE | 1 569 749 | 1/1971 |
| DE | 29 17 271 | 11/1980 |
| EP | 0 714 954 | 6/1996 |
| FR | 2 188 202 | 1/1974 |
| FR | 2 586 913 | 3/1987 |
| GB | 0 822 846 | 11/1959 |
| GB | 0 876 663 | 9/1961 |
| GB | 1 047 796 | 11/1966 |
| GB | 1 139 407 | 1/1969 |
| GB | 1 188 605 | 4/1970 |
| GB | 2 075 539 | 11/1981 |
| GB | 2 180 215 | 3/1987 |
| JP | 59-162553 | 9/1984 |
| JP | 62-201967 | 9/1987 |
| JP | 08179465 * | 7/1996 |
| WO | WO 95/01772 | 1/1995 |
| WO | WO 95/15144 | 6/1995 |
| WO | WO 01/66646 | 9/2001 |

OTHER PUBLICATIONS

English Abstract of the Japanese Patent No. (JP 08179465), dated Jul. 12, 1996.*

STIC Search Report.*

Barker et al., "Steric Effects in Di- and Tri-arylmethanes. Part IX. Electronic Absorption Spectra of Juloidine (2,3,6,7-Tetrahydro-1H, 5H-benzo[ij]quinolizine) and Kairoline (1-Methyl-1,2,3,4,-tetrahydroquinoline) Analogues of Michler's Hydrol Blue, Malachite Green, Crystal Violet, and Michler's Ketone," J. Chem. Soc. (B), pp. 1068-1071, 1969.

(Continued)

*Primary Examiner*—Eisa Elhilo
(74) *Attorney, Agent, or Firm*—Finnegan Henderson Farabow Garrett & Dunner LLP

(57) ABSTRACT

Composition for dyeing keratin fibers, for example, human keratin fibers such as the hair, which comprises at least one compound chosen from among the direct dyes of the heteroylarylmethane type defined herein, including diheteroylarylmethane and leuco precursors thereof. Furthermore, a method for dyeing keratin fibers, for example, human keratin fibers such as the hair, using the composition and a kit or device containing same.

34 Claims, No Drawings

OTHER PUBLICATIONS

Copending U.S. Appl. No. 10/745,634, filed Dec. 29, 2003.
Copending U.S. Appl. No. 10/746,497, filed Dec. 29, 2003.
English language Derwent Abstract of DE 1 254 118, May 22, 1968.
English language Derwent Abstract of DE 1 569 749, Jan. 21, 1971.
English language Derwent Abstract of DE 1 569 750, Apr. 24, 1967.
English language Derwent Abstract of DE 1 620 564, May 14, 1970.
English language Derwent Abstract of DE 29 17 271, Nov. 6, 1980.
English language Derwent Abstract of FR 2 188 202, Jan. 18, 1974.
English language Patent Abstracts of Japan Abstract of JP 59-162553, Sep. 13, 1984.
English language Derwent Abstract of JP 62-201967, Sep. 5, 1987.
French Search Report of French Patent Application No. 0216849, dated Sep. 3, 2003.
French Search Report of French Patent Application No. 0216851, dated Oct. 8, 2003.
French Search Report of French Patent Application No. 0216845, dated Nov. 21, 2003.
Office Action in co-pending U.S. Appl. No. 10/745,634, dated Oct. 20, 2005.
Office Action in co-pending U.S. Appl. No. 10/746,497, dated Oct. 20, 2005.
Shikhakiev: Izvestiya Vysshikh Uchebnykh Zavedenii, Khimiya I Khimicheskaya Tekhnologiya, vol. 42, No. 4, 1999, pp. 83-87.

* cited by examiner

COMPOSITION FOR DYEING KERATIN FIBERS COMPRISING A DEFINED DIHETEROYLARYLMETHANE DIRECT DYE OR A LEUCO PRECURSOR OF THIS DYE AND DYEING METHOD USING IT

This application claims the benefit of U.S. provisional application Ser. No. 60/450,358, filed Feb. 28, 2003.

An aspect of the present disclosure relates to a dyeing composition for keratin fibers, for example, human keratin fibers such as the hair, comprising at least one compound chosen from among the direct heteroylarylmethane type dyes defined herein, including diheteroylarylmethane and the leuco precursors thereof, the leuco prescursors herein also being referred to as dyes.

Furthermore, an aspect of the disclosure relates to a method for dyeing keratin fibers, for example, human keratin fibers such as the hair, that uses the composition.

Many compositions and many methods exist for dyeing keratin fibers, such as the human hair.

Thus, it is known how to dye keratin fibers such as the human hair with dyeing compositions containing oxidation dye precursors, including ortho and paraphenylenediamines, ortho and paraaminophenols, heterocyclic compounds, such as diaminopyrazole derivatives, generally called "oxidation bases". The precursors of oxidation dyes, and oxidation bases, are colorless or slightly colored compounds which, when associated with oxidizing products, can create colored and coloring compounds through an oxidation condensation process.

It is also known that the obtained color shades can be varied with these oxidation bases by associating them with color coupling agents or color modifiers, the latter being chosen, for example, from among aromatic metadiamines, metaaminophenols, metadiphenols, and certain heterocyclic compounds.

The variety of molecules involved, on the one hand at the level of the oxidation bases and, on the other hand, at the level of the coupling agents, makes it possible to obtain a wide range of colors.

So-called "permanent" coloration, obtained by these oxidation dyes can, moreover, satisfy at least one of a certain number of desirable characteristics, such as no toxicological problems, possibility of obtaining desired intensity of shades, and resistance to external agents, such as light, bad weather, washing, permanent waving, sweat, and rubbing.

In one aspect of the present disclosure, the dyes can also cover white hair and can be the least selective possible, making it possible to obtain the smallest possible color variation, along the length of a keratin fiber that in fact can have different sensitivities. In other words, the fiber can be damaged between its tip and its root leading to different sensitivities.

It is apparent that even if the standard base-coupler associations make it possible to obtain a wide range of colors, they may not able to satisfy at least one of the desirable characteristics listed above and, for example, may lead to the production of varied and poorly defined coupling products in the fiber, posing problems of safety and/or tenacity that can be difficult to control, as, for example, a selective color changing.

Another method for dyeing keratin fibers, such as the hair, is to use direct dyes.

The standard dyes used are dyes of the aromatic nitrated type, anthraquinonics, nitropyridinics, azoics, cationic azoics, xanthenics, acridinics azinics, triarylmethanes, nitrated benzenic, and natural dyes.

These dyes, comprising colored and coloring molecules with an affinity for fibers, are applied on the keratin fibers for the length of time needed to obtain the desired color and then rinsed.

The use of direct dyes is thus very widespread because they offer certain advantages relative to the precursors of oxidation dyes, such as reduction of potential risks of allergy and absence of sensitization of the hair due to the oxidizing process.

However, the colorations obtained can be temporary or semi-permanent, since the nature of the interactions linking direct dyes to the keratin fiber, and their desorption from the surface and/or the centre of the fiber can be responsible for low dyeing power and poor resistance to washing, bad weather, or sweat. Furthermore, those direct dyes are generally sensitive to light due to the low resistance of the chromophore relative to photochemical attacks, in time leading to fading of the hair coloration.

Therefore there is a need for a dye composition for keratin fibers, for example, human keratin fibers, such as the hair, that can have at least one of the following advantages: being safe, being totally compatible with keratin fibers, having low selectivity, providing a large variety of powerful colors, making it possible to obtain a fast and stable coloration of keratin fibers, and resisting external agents such as light, bad weather, washing, sweat, and rubbing, and also to subsequent treatments, such as permanent waving.

There is still a need for a dye composition capable of treating all sorts of keratin fibers, all hair types, for example white hair, even if this hair has undergone a previous treatment, such as a bleaching or permanent waving treatment. Finally, a need exists for a composition that produces the coloration without it being necessary to first carry out sensitization of the keratin fiber of the hair.

An aspect of the present disclosure is to provide a dye composition for keratin fibers, for example, human keratin fibers, such as the hair, that fulfils, among others, at least one of the needs set out above.

A further aspect of the present disclosure is to provide a composition for dyeing keratin fibers without at least one of the inconveniences, defects, limitations, and disadvantages of the dye compositions of the prior art, whether it is a matter of dye compositions involving a coupler-base association or compositions involving a direct dye.

An aspect of the disclosure is a composition for dyeing keratin fibers comprising, in a cosmetic medium suitable for dyeing, at least one dye chosen from formulae (I), (Ibis), (Iter), (II), and (IIbis), their tautomeric forms, and their addition salts:

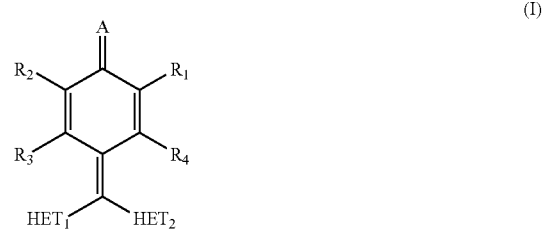

-continued

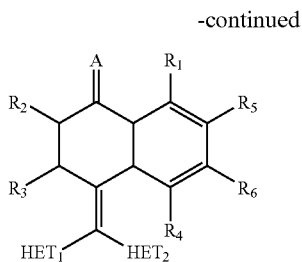
(Ibis)

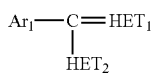
(Iter)

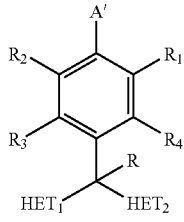
(II)

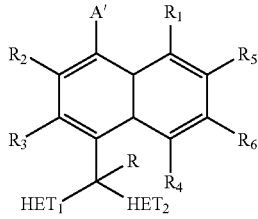
(IIbis)

in which:

A is chosen from O, NH, N-alkyl N-hydroxyalkyl; ammonium; N-alkylammonium; N-(hydroxyalkyl) ammonium; N,N-dialkylammonium, N,N-di(hydroxyalkyl) ammonium, and N-(hydroxyalkyl) N-(alkyl) ammonium, in which the two alkyl groups may form, together with the nitrogen atom to which they are linked, a cycle that may be interrupted by at least one atom chosen from nitrogen, oxygen, and sulphur;

$Ar_1$ is chosen from aryl, optionally substituted with at least one group Z, $HET_1$, $HET_2$, which may be the same or different, are chosen from heterocycle, optionally substituted with at least one group Z';

$R_1$ to $R_6$ and Z, Z', which may be the same or different, are chosen from hydrogen, halogen, such as F, Cl, Br, and I, —$NHSO_3H$; hydroxyl; alkyl; alkoxy; alkylthio; amino; monoalkylamino; and dialkylamino, in which the two alkyl groups may form, together with the nitrogen atom to which they are linked, a cycle that may be interrupted by at least one atom chosen from nitrogen, oxygen, and sulphur; heterocycle, nitro; aryl; acyl; alkoxycarbonyl; carboxamido; cyano; —$CO_2H$; —$SO_3H$; —$PO_3H_2$; and —$PO_4H_2$;

A' is chosen from hydrogen, hydroxyl, amino, (hydroxyalkyl)amino, di(hydroxyalkyl)amino, (hydroxyalkyl)(alkyl)amino, monoalkylamino, and dialkylamino, in which the two alkyl groups may form, together with the nitrogen atom to which they are linked, a cycle that may to be interrupted by at least one atom chosen from nitrogen, oxygen, and sulphur;

R is chosen from hydrogen, halogen; hydroxyl; alkoxy; and alkylthio.

In the formulae (I), (Ibis), (Iter), (II) and (IIbis), above, the term "alkyl" used for the alkyl radicals, as well as for the groups including an alkyl part, means, unless otherwise mentioned, carbon chains, straight and branched, having from 1 to 30 carbon atoms, such as from 1 to 8, and further such as from 1 to 4, that may be carried and/or interrupted by at least one atom chosen from of oxygen, sulphur, and nitrogen, and that may be substituted with at least one group chosen from halogen, such as chlorine, bromine, iodine and fluorine; heterocycle; aryl; hydroxyl; alkoxy; amino; acyl; carboxamido; —$CO_2H$; —$SO_3H$; —$PO_3H_2$; —$PO_4H_2$; —$NHSO_3H$; sulphonamide; monoalkylamino; trialkylammonium; and dialkylamino, in which the two alkyl groups may form, together with the nitrogen atom of said dialkyl ($C_1$–$C_4$)amino group, to which they are linked, a cycle that may be interrupted by at least one atom chosen from nitrogen, oxygen, and sulphur.

In the same way, according to the present disclosure, the term "alkoxy" used for the alkoxy radicals, as well as for the groups including an alkoxy part, means, unless otherwise mentioned, O-alkyl chains, the term alkyl having the meaning indicated above. The alkoxy radicals of the alkoxycarboyl groups have, for example, from 1 to 4 carbon atoms. Acyl groups have, for example, from 2 to 4 carbon atoms.

According to the present disclosure, the term "heterocycle" means cycle, aromatic and not, containing 5, 6, and 7 members, and from 1 to 3 heteroatoms chosen from nitrogen, sulphur, and oxygen. These heterocycles can be condensed on other heterocycles or on other cycles, especially aromatic cycles, such as phenyl. These heterocycles can, furthermore, be quaternized by an alkyl radical. The terms "alkyl" and "alkoxy" have the meanings indicated above.

According to an advantageous embodiment of the invention, the $HET_1$ and $HET_2$ are chosen from unsaturated heterocycle, such as aromatic heterocycle optionally substituted with at least one Z'.

Among the heterocycle, such as $HET_1$ and $HET_2$, the following non-limiting cycles may be mentioned as examples: thiophene, benzothiophene, furane, benzofurane, indole, indoline, carbazole, pyridine, dehydroquinoline, chromone, julolidine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

According to the disclosure, it is meant by "aryl," unless otherwise mentioned, $C_6$ to $C_{30}$ aryl that may be substituted with at least one substituent chosen from alkyl; alkoxy; acyl; cyano; carboxamido; —$CO_2H$; —$SO_3H$: —$PO_3H_2$; —$PO_4H_2$: hydroxyl; amino; monoalkyl($C_1$–$C_4$)amino; and dialkyl($C_1$–$C_4$)amino; in which the two alkyl groups may form, together with the nitrogen atom of the dialkyl($C_1$–$C_4$) amino, to which they are linked, a cycle that may be interrupted by at least one atom chosen from nitrogen, oxygen, and sulphur. For example, aryl is chosen from phenyl and naphthyl that may be substituted as described above.

In the formula (Iter), $Ar_1$ may be, for example, a phenyl, and as a further example, $Ar_1$ is not substituted, i.e., Z=H.

In the formula (Iter), $HET_1$ is, for example, linked to the carbon atom bearing $Ar_1$ and $HET_2$ through a carbon atom of said $HET_1$ cycle.

The compounds (I), (Ibis) and (Iter) can be defined as being direct dyes of the diheteroylarylmethane type and the compounds of formulae (II) and (IIbis) are the leuco precursors of the diheteroylarylmethane of formulae (I), (Ibis), and (Iter).

The leuco (II) and (IIbis) compounds are generally slightly colored or not at all colored and can be converted by simple oxidation in the air or in the presence of an oxidizing agent to a diheteroylarylmethane compound of formula (I), (Ibis), and (Iter).

As examples of formulae (I), (Ibis), (Iter), (II), and (IIbis) able to be used within the scope of the present disclosure, the following non-limiting compounds can be mentioned for which the counter ions are specified or not, and their addition salts:

4-[Bis-(2-methyl-1H-indol-3-yl)-methylene]-cyclohexa-2,5-dienylidene}-dimethyl-ammonium;

1,2,2,4-Tetramethyl-6-[phenyl-(1,2,2,4-tetramethyl-1,2,3,4-tetrahydro-quinolin-6-yl)-methylene]-2,3,4,6-tetrahydroquinolinium chloride;

1,2,2,3-Tetramethyl-5-[(1-methyl-2-phenyl-1H-indol-3-yl)-phenyl-methylene]-3,5-dihydro-2H-indolinium chloride;

9-Ethyl-3-[(9-ethyl-9H-carbazol-3-yl)-phenyl-methylene]-3H-carbazolium chloride;

1-Ethyl-3-[(1-ethyl-2-methyl-1H-indol-3-yl)-p-tolyl-methylene]-2-methyl-3a,7a-dihydro-3H-indolium;

6-{(4-Nitro-phenyl)-[1-(4-sulfo-butyl)-1,2,3,4-tetrahydro-quinolin-6-yl]-methylen}-1-(4-sulfo-butyl)-2,3,4,6-tetrahydro-quinolinium;

6-{(4-Cyano-phenyl)-[1-(4-sulfo-butyl)-1,2,3,4-tetrahydro-quinolin-6-yl]-methylen}-1-(4-sulfo-butyl)-2,3,4,6-tetrahydro-quinolinium;

Diethyl-{4-[(2-methyl-1H-indol-3-yl)-thiophen-2-yl-methylene]-cyclohexa-2,5-dienylidene}-ammonium;

1-Ethyl-3-[(1-éthyl-2-methyl-1H-indol-3-yl)-(4-methoxy-phenyl)-methylene]-2-methyl-3a,7a-dihydro-3H-indolium;

Ethanaminium, N-[4-[(3-carboxypyrazinyl)(1-ethyl-2-methyl-1H-indol-3-yl)methylene]-3-ethoxy-2,5-cyclohexadien-1-ylidene]-N-ethyl-, internal salt;

Ethanaminium, N-[4-[(3-carboxypyrazinyl)(1-ethyl-2-methyl-1H-indol-3-yl)methylene]-3-ethoxy-2,5-cyclohexadien-1-ylidene]-N-ethyl-, chloride;

Cyclohepta[b]furylium, 3-[[4-(dimethylamino)phenyl](2-oxo-2H-cyclohepta[b]furan-3-yl)methylene]-2,3-dihydro-2-oxo;

Methanaminium, N-[4-[bis(1,2,3,4,10,14b-hexahydro-2-methyldibenz[c,f]pyrazino[1,2-a]azepin-8-yl)methylene]-2,5-cyclohexadien-1-ylidene]-N-methyl-, perchlorate, diperchlorate;

Methanaminium, N-[4-[bis(1,2,3,4,10,14b-hexahydro-2-methyldibenzo [c,f]pyrazino[1,2-a]azepin-8-yl)methylene]-2,5-cyclohexadien-1-ylidene]-N-methyl-, perchlorate;

Methanaminium, N-[4-[bis(1,2,3,4,10,14b-hexahydro-2-methyldibenzo [c,f]pyrazino[1,2-a]azepin-8-yl)methylene]-2,5-cyclohexadien-1-ylidene]-N-methyl-;

Methanaminium, N-[4-[bis(2,3-dihydro-1,5-dimethyl-3-oxo-2-phenyl-1H-pyrazol-4-yl)methylene]-2,5-cyclohexadièn-1-ylidene]-N-methyl-;

Morpholinium, 4-[5-[[4-(dimethylamino)phenyl][5-(4-morpholinyl)-2-thienyl]methylene]-2(5H)-thienylidene]-, perchlorate;

Morpholinium, 4-[5-[[4-(dimethylamino)phenyl][5-(4-morpholinyl)-2-thienyl]methylene]-2(5H)-thienylidene]-;

1H-Indolizinium, 7-(dimethylamino)-1-[[7-(dimethylamino)-3-(ethoxycarbonyl)-1-indolizinyl][4-(dimethylamino)phenyl]methylene]-3-(ethoxycarbonyl)-, perchlorate;

1H-Indolizinium, 7-(dimethylamino)-1-[[7-(dimethylamino)-3-(ethoxycarbonyl)-1-indolizinyl][4-(dimethylamino)phenyl]methylene]-3-(ethoxycarbonyl)-;

Cyclohepta[b]pyrrolium, 3-[(1,2-dihydro-2-oxo-1-phenylcyclohepta[b]pyrrol-3-yl)[4-(dimethylamino)phenyl]methylene]-2,3-dihydro-2-oxo-1-phenyl-, hexafluorophosphate;

Cyclohepta[b]pyrrolium, 3-[(1,2-dihydro-2-oxo-1-phenylcyclohepta[b]pyrrol-3-yl)[4-(dimethylamino)phenyl]methylene]-2,3-dihydro-2-oxo-1-phenyl-;

Quinolinium, 6-[[4-(dimethylamino)phenyl](1,2,3,4-tetrahydro-1,2,2,4-tetramethyl-6-quinolinyl)methylene]-2,3,4,6-tetrahydro-1,2,2,4-tetraméthyl-, chloride;

Quinolinium, 6-[(1,2-dihydro-1,2,2,4-tetraméthyl-6-quinolinyl)[4-(dimethylamino)phenyl]methylene]-2,6-dihydro-1,2,2,4-tetramethyl-, chloride;

3H-Carbazolium, 9-ethyl-3-[(9-ethyl-9H-carbazol-3-yl)[4-(methylphenylamino)phenyl]methylene]-, tetrafluoroborate(1-);

3H-Carbazolium, 3-[[4-(dimethylamino)phenyl](9-ethyl-9H-carbazol-3-yl)methylene]-9-ethyl-, tetrafluoroborate (1-);

3H-Carbazolium, 9-ethyl-3-[(9-ethyl-9H-carbazol-3-yl)[4-(methylphenylamino)phenyl]methylene]-, perchlorate;

3H-Carbazolium, 9-ethyl-3-[(9-ethyl-9H-carbazol-3-yl)[4-(methylphenylamino)phenyl]methylene]-, bromide;

3H-Carbazolium, 9-ethyl-3-[(9-ethyl-9H-carbazol-3-yl)[4-(methylphenylamino)phenyl]methylene]-, chloride;

3H-Carbazolium, 3-[[4-(dimethylamino)phenyl](9-ethyl-9H-carbazol-3-yl)methylene]-9-ethyl-, bromide;

3H-Carbazolium, 3-[[4-(dimethylamino)phenyl](9-ethyl-9H-carbazol-3-yl)methylene]-9-ethyl-, chloride;

3H-Carbazolium, 9-ethyl-3-[(9-ethyl-9H-carbazol-3-yl)[4-(methylphenylamino)phenyl]methylene]-, iodide;

3H-Carbazolium, 3-[[4-(dimethylamino)phenyl](9-ethyl-9H-carbazol-3-yl)methylene]-9-ethyl-, iodide;

3H-Carbazolium, 3-[[4-(dimethylamino)phenyl](9-ethyl-9H-carbazol-3-yl)methylene]-9-ethyl-, perchlorate;

1H-Pyrazolium, 4-[(2,3-dihydro-1,5-dimethyl-3-oxo-2-phenyl-1H-pyrazol-4-yl)[4-(trimethylammonio) phenyl]methylene]-4,5-dihydro-2,3-dimethyl-5-oxo-1-phenyl-, diperchlorate;

1H-Pyrazolium, 4-[(2,3-dihydro-1,5-dimethyl-3-oxo-2-phenyl-1H-pyrazol-4-yl)[4-(trimethylammonio)phenyl]methylene]-4,5-dihydro-2,3-dimethyl-5-oxo-1-phenyl-;

5H-Benzo[a]carbazolium, 11-ethyl-5-[(11-ethyl-3-methoxy-8-methyl-11H-benzo[a]carbazol-5-yl)(4-nitrophenyl)methylene]-3-methoxy-8-methyl-, tetrafluoroborate;

5H-Benzo[a]carbazolium, 11-ethyl-5-[(11-ethyl-3-methoxy-8-methyl-11H-benzo[a]carbazol-5-yl)(4-nitrophenyl)methylene]-3-methoxy-8-methyl-;

5H-Benzo[a]carbazolium, 11-ethyl-5-[(11-ethyl-2-methoxy-8-methyl-11H-benzo[a]carbazol-5-yl)(4-nitrophenyl)methylene]-2-methoxy-8-methyl-, tetrafluoroborate;

5H-Benzo[a]carbazolium, 11-ethyl-5-[(11-ethyl-2-methoxy-8-methyl-11H-benzo[a]carbazol-5-yl)(4-nitrophenyl)methylene]-2-methoxy-8-methyl-;

5H-Benzo[a]carbazolium, 11-ethyl-5-[(11-ethyl-8-methoxy-11H-benzo[a]carbazol-5-yl)(4-nitrophenyl)methylene]-8-methoxy-, tetrafluoroborate;

5H-Benzo[a]carbazolium, 11-ethyl-5-[(11-ethyl-8-methoxy-11H-benzo[a]carbazol-5-yl)(4-nitrophenyl)methylene]-8-methoxy-;

5H-Benzo[a]carbazolium, 11-ethyl-5-[(11-ethyl-4-methoxy-11H-benzo[a]carbazol-5-yl)(4-nitrophenyl)methylene]-4-methoxy-, tetrafluoroborate;

5H-Benzo[a]carbazolium, 11-ethyl-5-[(11-ethyl-4-methoxy-11H-benzo[a]carbazol-5-yl)(4-nitrophenyl)methylene]-4-methoxy-;

5H-Benzo[a]carbazolium, 11-ethyl-5-[(11-ethyl-3-methoxy-11H-benzo[a]carbazol-5-yl)(4-nitrophenyl)methylene]-3-methoxy-, tetrafluoroborate;

5H-Benzo[a]carbazolium, 11-ethyl-5-[(11-ethyl-3-methoxy-11H-benzo[a]carbazol-5-yl)(4-nitrophenyl)methylene]-3-methoxy-;

5H-Benzo[a]carbazolium, 11-ethyl-5-[(11-ethyl-2-methoxy-11H-benzo[a]carbazol-5-yl)(4-nitrophenyl)methylene]-2-methoxy-, tetrafluoroborate;

5H-Benzo[a]carbazolium, 11-ethyl-5-[(11-ethyl-2-methoxy-11H-benzo[a]carbazol-5-yl)(4-nitrophenyl)methylene]-2-methoxy-;

5H-Benzo[a]carbazolium, 5-[(2-chloro-4-nitrophenyl)(11-ethyl-11H-benzo[a]carbazol-5-yl)methylene]-11-ethyl-, salt with trifluoromethanesulfonic acid (1:1);

5H-Benzo[a]carbazolium, 5-[(2-chloro-4-nitrophenyl)(11-ethyl-11H-benzo[a]carbazol-5-yl)methylene]-11-ethyl;

5H-Benzo[a]carbazolium, 11-ethyl-5-[(11-ethyl-11H-benzo[a]carbazol-5-yl)(4-nitrophenyl)methylene]-, tetrafluoroborate;

5H-Benzo[a]carbazolium, 11-ethyl-5-[(11-ethyl-11H-benzo[a]carbazol-5-yl)(4-nitrophenyl)methylene]-;

5H-Benzo[a]carbazolium, 5-[[4-(diethylamino)phenyl](11-ethyl-11H-benzo[a]carbazol-5-yl)methylene]-11-ethyl-, tetrafluoroborate(1-);

5H-Benzo[a]carbazolium, 5-[[4-(diethylamino)phenyl](11-ethyl-11H-benzo[a]carbazol-5-yl)methylene]-11-ethyl-;

5H-Benzo[a]carbazolium, 5-[[4-(dimethylamino)phenyl](11-ethyl-11H-benzo[a]carbazol-5-yl)methylene]-11-ethyl-, tetrafluoroborate(1-);

5H-Benzo[a]carbazolium, 5-[[4-(dimethylamino)phenyl](11-ethyl-11H-benzo[a]carbazol-5-yl)methylene]-11-ethyl-;

Salt of 1H-Pyrazolium, 4-[(2,3-dihydro-1,5-dimethyl-3-oxo-2-phenyl-1H-pyrazol-4-yl)[4-(dimethylamino)phenyl]methylene]-4,5-dihydro-2,3-dimethyl-5-oxo-1-phenyl- and a monoacid;

3H-Carbazolium, 3-[[4-[bis(phenylmethyl)amino]phenyl](9-ethyl-9H-carbazol-3-yl)methylene]-9-ethyl-, iodide;

3H-Imidazo[1,2-a]benzimidazolium, 3-[[4-(dimethylamino)phenyl](9-methyl-2-phenyl-9H-imidazo[1,2-a]benzimidazol-3-yl)methylene]-9-methyl-2-phenyl-, chloride;

3H-Imidazo[1,2-a]benzimidazolium, 3-[[4-(dimethylamino)phenyl](2,9-dimethyl-9H-imidazo[1,2-a]benzimidazol-3-yl)methylene]-2,9-dimethyl-, bromide;

1H-Pyrazolium, 4-[(2,3-dihydro-1,5-dimethyl-3-oxo-2-phenyl-1H-pyrazol-4-yl)[4-(dipropylamino)phenyl]methylene]-4,5-dihydro-2,3-dimethyl-5-oxo-1-phenyl-;

1H-Pyrazolium, 4-[[4-(diethylamino)phenyl](2,3-dihydro-1,5-dimethyl-3-oxo-2-phenyl-1H-pyrazol-4-yl)methylene]-4,5-dihydro-2,3-dimethyl-5-oxo-1-phenyl-;

1H-Pyrazolium, 4-[(2,3-dihydro-1,5-dimethyl-3-oxo-2-phenyl-1H-pyrazol-4-yl)(4-nitrophenyl)methylene]-4,5-dihydro-2,3-dimethyl-5-oxo-1-phenyl-;

1H-Pyrazolium, 4-[(2,3-dihydro-1,5-dimethyl-3-oxo-2-phenyl-1H-pyrazol-4-yl)[4-(dimethylamino)phenyl]methylene]-4,5-dihydro-2,3-dimethyl-5-oxo-1-phenyl-;

1H-Pyrazolium, 4-[(4-aminophenyl)(2,3-dihydro-1,5-dimethyl-3-oxo-2-phenyl-1H-pyrazol-4-yl)methylene]-2,3-dimethyl-5-oxo-1-phenyl;

3H-Indolizinium, 3-[[4-(dimethylamino)phenyl](6-ethenyl-1,2-dimethyl-3-indolizinyl)methylene]-6-ethenyl-1,2-dimethyl-;

3H-Indolizinium, 3-[p-(dimethylamino)-α-(6-ethyl-1,2-dimethyl-3-indolizinyl)benzylidene]-6-ethyl-1,2-dimethyl-, iodide;

3H-Indolizinium, 3-[p-(dimethylamino)-α-(1,2-dimethyl-6-vinyl-3-indolizinyl)benzylidene]-1,2-dimethyl-6-vinyl-, perchlorate;

2-Pyrazolinium, 4-(p-amino-α-antipyrinylbenzylidene)-2,3-dimethyl-5-oxo-1-phenyl-, perchlorate;

2-Pyrazolinium, 4-(α-antipyrinyl-p-nitrobenzylidene)-2,3-dimethyl-5-oxo-1-phenyl-, perchlorate;

2-Pyrazolinium, 4-[α-antipyrinyl-p-(diethylamino)benzylidene]-2,3-dimethyl-5-oxo-1-phenyl-, perchlorate;

2-Pyrazolinium, 4-[α-antipyrinyl-p-(dimethylamino)benzylidene]-2,3-dimethyl-5-oxo-1-phenyl-, perchlorate;

Methylium, bis[6-(dimethylamino)-3-methyl-1H-indol-2-yl][4-(dimethylamino)phenyl]-, perchlorate;

Methylium, bis[6-(dimethylamino)-3-methyl-1H-indol-2-yl][4-(dimethylamino)phenyl]-

Methylium, bis[6-(dimethylamino)-3-methyl-1H-indol-2-yl](4-nitrophenyl)-, perchlorate;

Methylium, bis[6-(dimethylamino)-3-methyl-1H-indol-2-yl](4-nitrophenyl)-;

Methylium, bis(benzo[b]thien-2-yl)[4-(dimethylamino)phenyl]-, tetrafluoroborate

Methylium, bis(benzo[b]thien-2-yl)[4-(dimethylamino)phenyl]-;

Methylium, [4-(dimethylamino)phenyl]bis(1-methyl-1H-pyrrol-2-yl)-, tetrafluoroborate;

Methylium, [4-(dimethylamino)phenyl]bis(1-methyl-1H-pyrrol-2-yl)-;

Diantipyrinyl(p-nitrophenyl)methylium perchlorate;

Methylium, bis(9,10-dihydro-9,9,10-trimethyl-3-acridinyl)[4-(dimethylamino)phenyl]-, chloride;

Methylium, [4-(dimethylamino)phenyl]bis(10-methyl-10H-phenothiazin-2-yl)-, chloride;

3H-Pyrazol-3-one, 4,4'-[[4-(dimethylamino)phenyl]methylene]bis[1,2-dihydro-1,5-dimethyl-2-phenyl-, mono[tetrafluoroborate(1-)];

[3H-Pyrazol-3-one, 4,4'-[[4-(dimethylamino)phenyl]methylene]bis[1,2-dihydro-1,5-dimethyl-2-phenyl-, bis[tetrafluoroborate(1-)];

Salt of 3H-Pyrazol-3-one, 4,4'-[[4-(dimethylamino)phenyl]methylene]bis[1,2-dihydro-1,5-dimethyl-2-phenyl- and a diacid;

Salt of 3H-Pyrazol-3-one, 4,4'-[[4-(dimethylamino)phenyl]methylene]bis[1,2-dihydro-1,5-dimethyl-2-phenyl-, and a monoacid;

Quinolinium, 4,4'-[(4-nitrophenyl)methylene]bis[1-ethyl-, dichloride;

Methylium, bis(9-ethyl-9H-carbazol-3-yl)(4-nitrophenyl)-, iodide;

Methylium, [4-(dimethylamino)phenyl]bis(9-ethyl-9H-carbazol-3-yl)-, iodide;

Methylium, 9H-carbazol-3-yl[4-(dimethylamino)phenyl](6-methyl-9H-carbazol-3-yl)-;

Quinolizinium, 2,2'-[(4-nitrophenyl)methylene]bis[1,2,3,4-tetrahydro-1-oxo-;

Methylium, 9H-carbazol-3-yl[4-(dimethylamino)phenyl](6-methyl-9H-carbazol-3-yl)-, tetrafluoroborate;

Borate(1-), tetrafluoro-, 9H-carbazol-3-yl[4-(dimethylamino)phenyl](6-methyl-9H-carbazol-3-yl)methylium;

6-Methyl-3,3'-dicarbazolyl-p-dimethylaminophenylmethyl fluoroborate;

6,6'-Dichloro-9,9'-dibutyl-3,3'-dicarbazolyl-p-nitrophenylmethyl chlorure;

Quinolizinium, 2,2'-(p-nitrobenzylidene)bis[1,2,3,4-tetrahydro-1-oxo-,dipicrate;

Picric acid salt of 2,2'-(p-nitrobenzylidene)bis[1,2,3,4-tetrahydro-1-oxoquinolizinium];

Quinolizinium, 2,2'-(p-nitrobenzylidene)bis[1,2,3,4-tétrahydro-1-oxo-, diperchlorate;

Benzylium, p-(diethylamino)-α,α-bis(2,3-dimethyl-5-oxo-1-phenyl-3-pyrazolin-4-yl)-;

Benzylium, α,α-diantipyrinyl-p-(dimethylamino)-;

Benzylium, α,α-bis(2,3-dimethyl-5-oxo-1-phenyl-3-pyrazolin-4-yl)-p-nitro-; and

Benzylium, p-amino-α,α-di-4-antipyrinyl-.

The diheteroylarylmethanes of formulae (I), (Ibis), and (Iter) and the leuco compounds of formulae (II) and (IIbis) are known compounds. These compounds can be prepared according to synthesis methods well known to those skilled in the art and in documents, for example, DE-A-1-569 750, FR-A-2 188 202, U.S. Pat. No. 3,995,088, U.S. Pat. No. 4,154,463, U.S. Pat. No. 4,355,823, U.S. Pat. No. 5,094,688, U.S. Pat. No. 5,266,699 and U.S. Pat. No. 5,362,612, all of which are herein incorporated by reference in their entirety.

It is apparent that at least some compositions according to the disclosure can make it possible, unexpectedly, to obtain intense colorations, even on non-sensitized hair.

At least some of the compositions according to the disclosure make it possible to obtain chromatic, as well as dark varied glints, very powerful, not very selective, and tenacious colors.

Thus, diheteroylarylmethane dyes of formulae (I), (Ibis), and (Iter) and the leucos of formulae (II) and (IIbis) included in the compositions according to the disclosure, can make it possible to obtain all shades from green to blue, passing through the reds. For example, they also make it possible to obtain shades of black.

The colorations obtained with the compositions according to the disclosure can be at least one of tenacious, stable and resistant, relative to bad weather, washing, sweat, rubbing, and subsequent treatments, such as permanent waving.

For example, these colorations can be especially resistant to light.

The compounds of formulae (I), (Ibis), (Iter), (II), (IIbis) above and/or their additive salt(s) generally represent, for example, from about 0.0001 to about 10% by weight of the total weight of the dye composition, such as from about 0.005 to about 10% by weight and, even further such as from about 0.01 to about 6% by weight of the total weight of the dye composition according to the disclosure.

The dye composition according to the disclosure may further contain at least one direct dye different from formulae (I), (Ibis), (Iter), (II), and (IIbis). The at least one different direct can, for example, be chosen from among neutral, acid, and cationic benzenic nitrated direct dyes, neutral, acid, and cationic azoic direct dyes, quinonic direct dyes, such as neutral, acid, and cationic anthraquinonic direct dyes, azinic direct dyes, triarylmethanic direct dyes, indoaminic direct dyes, and natural direct dyes.

Among the aromatic direct dyes, the following compounds can be mentioned, in a non-limiting manner:

1,4-diamino-2-nitrobenzene;
1-amino-2nitro-4-β-hydroxyethylaminobenzene;
1-amino-2nitro-4-bis(β-hydroxyethyl)-aminobenzene;
1,4-Bis(β-hydroxyethylamino)-2-nitrobenzene;
1-β-hydroxyethylamino-2-nitro-4-bis-(β-hydroxyethylamino)-benzene;
1-β-hydroxyethylamino-2-nitro-4-aminobenzene;
1-β-hydroxyethylamino-2-nitro-4-(ethyl)(β-hydroxyethyl)-aminobenzene;
1-amino-3-methyl-4-β-hydroxyethylamino-6-nitrobenzene;
1-amino-2-nitro-4-β-hydroxyethylamino-5-chlorobenzene;
1,2-Diamino-4-nitrobenzene;
1-amino-2-β-hydroxyethylamino-5-nitrobenzene;
1,2-Bis-(β-hydroxyethylamino)-4-nitrobenzene;
1-amino-2-tris-(hydroxymethyl)-methylamino-5-nitrobenzene;
1-Hydroxy-2-amino-5-nitrobenzene;
1-Hydroxy-2-amino-4-nitrobenzene;
1-Hydroxy-3-nitro-4-aminobenzene;
1-Hydroxy-2-amino-4,6-dinitrobenzene;
1-β-hydroxyethyloxy-2-β-hydroxyethylamino-5-nitrobenzene;
1-Methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-Hydroxy-2-chloro-6-ethylamino-4-nitrobenzene;
1-Hydroxy-2-chloro-6-amino-4-nitrobenzene;
1-Hydroxy-6-bis-(β-hydroxyethyl)-amino-3-nitrobenzene;
1-β-hydroxyethylamino-2-nitrobenzene;
1-Hydroxy-4-β-hydroxyethylamino-3-nitrobenzene.

Among the azoic direct dyes, mention can be made of the cationic azoic dyes described in the patent applications WO-95/15144, WO-95/01772, EP-714954 and WO-A-01/66646, the disclosures of which related to such azoic direct dyes are specifically incorporated herein by reference.

Among these compounds, the following compounds can be mentioned in particular:

1,3-dimethyl-2-[[4-(dimethylamino)phenyl]azo]-1H-Imidazolium chloride;
1,3-dimethyl-2-[(4-aminophenyl)azo]-1H-Imidazolium chloride;
1-methyl-4-[(methylphenylhydrazono)methyl]-pyridinium methylsulphate.

Among the azoic direct dyes, the following dyes can also be mentioned, described in the INTERNATIONAL COLOR INDEX, 3rd edition:

Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24;
Disperse Black 9.

Mention can also be made of 1-(4'-aminodiphenylazo)-2-methyl-4bis-(β-hydroxyethyl)aminobenzene and 4-hydroxy-3-(2-methoxyphenylazo)-1-naphthalene sulphonic acid.

Among the quinonic direct dyes, the following dyes can be mentioned:

Disperse Red 15;
Solvent Violet 13;
Acid Violet 43;
Disperse Violet 1;

Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99, as well as the following compounds:
1-N-methylmorpholiniumpropylamino-4-hydroxyanthraquinone;
1-Aminopropylamino-4-methylaminoanthraquinone;
1-Aminopropylaminoanthraquinone;
5-β-hydroxyethyl-1,4-diaminoanthraquinone;
2-Aminoethylaminoanthraquinone;
1,4-Bis-(β,γ-dihydroxypropylamino)-anthraquinone.

Among the azinic dyes, the following compounds can be mentioned:
Basic Blue 17;
Basic Red 2.

Among the triarylmethanic dyes, the following compounds can be mentioned:
Basic Green 1;
Acid blue 9;
Basic Violet 3;
Basic Violet 14;
Basic Blue 7;
Acid Violet 49;
Basic Blue 26;
Acid Blue 7.

Among the indoaminic dyes, the following compounds can be mentioned:
2-β-hydroxyethlyamino-5-[bis-(β-4'-hydroxyethyl)amino]anilino-1,4-benzoquinone;
2-β-hydroxyethylamino-5-(2'-methoxy-4'-amino)anilino-1,4-benzoquinone;
3-N(2'-Chloro-4'-hydroxy)phenyl-acetylamino-6-methoxy-1,4-benzoquinone imine;
3-N (3'-Chloro-4'-methylamino)phenyl-ureido-6-methyl-1,4-benzoquinone imine;
3-[4'-N-(Ethyl,carbamylmethyl)-amino]-phenyl-ureido-6-methyl-1,4-benzoquinone imine.

Representative natural direct dyes that can be used according to the disclosure include: lawson, juglon, alizarin, purpurin, carminic acid, kermesic acid, purpurogallin, protocatechaldehyde, indigo, isatin, curcumin, spinulosin, and apigenidin. It is also possible to use extracts and decoctions containing these natural dyes and, for example, poultices and extracts with a henna base.

The additional at least one direct dye) different from the at least one dye chosen from formulae (I), (Ibis), (Iter), (II), and (IIbis) represents, for example, from about 0.001 to about 20% by weight of the total weight of the composition ready for use, such as from about 0.005 to about 10% by weight.

The composition according to the present disclosure may further comprise at least one oxidation base and optionally at least one coupler, such as those conventionally used for oxidation dyeing.

Examples of oxidation bases include paraphenylenediamines, bis-phenylalkylenediamines, para-aminophenols, ortho-aminophenols, heterocyclic bases, and their addition salts.

For example, couplers may include metaphenylenediamine couplers, meta-aminophenol couplers, metadiphenol couplers, naphthalenic couplers, heterocyclic couplers, and their addition salts.

When they are present, the at least one oxidation base and at least one coupling agent are each present generally, for example, in an amount from about 0.001 to about 10% by weight of the total weight of the dye composition, such as from about 0.005 to about 6%.

The medium suitable for dyeing, also called dyeing support, is generally chosen from water and a mixture of water and at least one organic solvent to solubilize the compounds that would not be sufficiently soluble in water. As an example of organic solvent, mention can be made of the lower alkanols in $C_1$–$C_4$, such as ethanol and isopropanol; the polyols and ethers of polyols, such as 2-butoxyethanol, propyleneglycol, propyleneglycol monomethylether, diethyleneglycol monoethyl ether, and monomethylether, as well as aromatic alcohols, such as benzylic alcohol and phenoxyethanol, and their mixtures.

The solvents may be present in proportions, for example, from about 1 to about 40% by weight relative to the total weight of the dye composition, such as from about 5 to about 30% by weight.

The dye composition in accordance with the disclosure can also include various additives conventionally used in compositions for dyeing hair, such as amphoteric, zwitterionic, anionic, cationic, and non-ionic surfactants and mixtures thereof, amphoteric, anionic, zwitterionic, cationic, and non-ionic polymers and mixtures thereof, mineral and organic thickening agents, such as anionic, cationic, non-ionic, and amphoteric polymer associative thickeners, antioxidizing agents, penetration agents, sequestering agents, fragrances, buffers, dispersing agents, conditioners, such as, for example, volatile and non-volatile silicones, modified and non-modified, film forming agents, ceramides, preserving agents, and opacifying agents.

These additives cited above are each in general present in an amount, for example, from about 0.01 to about 20% by weight relative to the weight of the composition.

For example, the compositions can contain a solvent chosen from among the alkanols in $C_2$–$C_4$ and the polyols of molecular weight lower than about 1000.

As a further example, the compositions contain at least one surfactant and/or at least one thickening agent chosen from mineral and organic thickening agents.

It is evident that one skilled in the art will take care to chose this or these optional additional compound or compounds in such a way that at least one advantageous property attached intrinsically to the oxidation dye composition according to the disclosure is not, or substantially not, damaged by the envisaged additive or additives.

The pH of the dye composition according to the disclosure in general, for example, ranges from about 3 to about 12, such as from about 5 to about 11, and even further such as from about 6 to about 8.5.

The pH can be adjusted to the desired value by acidifying or alkalizing agents commonly used for dyeing keratin fibers, as well as with the aid of standard buffering systems.

Exemplary acidifying agents include mineral and organic acids, such as hydrochloric acid, orthophosphoric acid, sulphuric acid, and carboxylic acids, such as acetic acid, tartric acid, citric acid, lactic acid, and sulphonic acid.

Exemplary alkalizing agents include ammonia, alkaline carbonates, alkanolamines, such as the mono- di- and triethanolamines, as well as their derivatives, hydroxides of sodium and potassium and the following compounds of formula (III):

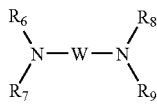

in which W is a propylene moiety optionally substituted with at least one substituent chosen from hydroxyl and alkyl in $C_1-C_4$; $R_6$, $R_7$, $R_8$ and $R_9$, which may be identical or different, are chosen from hydrogen, alkyl in $C_1-C_4$, and hydroxyalkyl in $C_1-C_4$.

The dyeing composition according to the invention may be under various forms, such as in the form of liquids, creams, gels, or in any other suitable form to carry out the dyeing of keratin fibers, such as human hair.

An aspect of the disclosure is also aimed at a method for the direct dyeing of keratin fibers, such as human keratin fibers, further such as hair, comprising the application on the keratin fibers of at least one dye composition comprising at least one dye chosen from formulae (I), (Ibis), (Iter), (II), and (IIbis), as defined herein. After a pause time (exposure time) is observed, the keratin fibers are rinsed, allowing the colored fibers to appear. The pause time (exposure time) is generally from about 3 to about 50 minutes, such as from about 5 to about 30 minutes.

It should be noted that coloring or direct dyeing (tinting) means coloring carried out without an oxidizing agent apart from the oxygen in the air.

When the dye composition comprises at least one dye chosen either from formulae (II) and (IIbis), defined herein, or from formulae (I), (Ibis), and (Iter), defined herein, and at least one oxidation base, and optionally at least one coupling agent, the dye composition may also contain an oxidizing agent.

Therefore, an embodiment of the disclosure is also a method for dyeing keratin fibers, such as human keratin fibers, such as the hair, in which at least one dye composition is applied on the fibers, the composition comprising at least one dye chosen either from formulae (II) and (IIbis), defined herein, or from formulae (I), (Ibis), and (Iter), defined herein, and at least one oxidation base, and optionally at least one coupler, the color being developed at acid, neutral or alkaline pH, using at least one oxidizing agent.

Representative oxidizing agents include hydrogen peroxide, urea peroxide, alkaline metal bromates, persalts, such as perborates and persulphates, peracids, and the oxidase enzymes among which can be mentioned peroxydases, oxydo-reductases with 2 electrons, such as uricases, and oxygenases with 4 electrons, such as the laccases. Hydrogen peroxide may be chosen.

The oxidizing agent may be added to the composition according to the invention just at the time of use or it may be added starting from an oxidizing composition containing it, applied simultaneously or sequentially with the composition according to the disclosure. The oxidizing composition may also include various additives conventionally used in compositions for dyeing hair and such as those defined above. If there is a mixture with the dye composition, the pH of the oxidizing composition including the oxidizing agent is such that after mixing with the dye composition, the pH of the resulting composition applied on the keratin fibers varies, for example, from about 3 to about 12, such as from about 5 to about 11, and even further such as from about 6 to about 8.5. The pH can be adjusted to the desired value by acidifying or alkalizing agents normally used in dyeing keratin fibers, such as those defined herein.

The composition that is finally applied on the keratin fibers can take various forms, such as a liquid form, creams, gels or any other appropriate form suitable for carrying out dyeing of keratin fibers, such as human hair.

Another aspect of the disclosure is a device or kit with at least two separate compartments, sometimes called a "dyeing kit", in which a first compartment comprises a dye composition as defined herein, comprising at least one dye chosen either from formulae (II) and (IIbis), defined above, or from formulae (I), (Ibis), and (Iter), defined above, and at least one oxidation base, and optionally at least one coupling agent, and in which a second compartment comprises an oxidizing composition.

This device can be equipped with a device to deliver the desired mixture on the hair, such as the devices described in FR-2 586 913.

In the case of a composition containing at least one dye chosen from formulae (II) and (IIbis), it is desirable to avoid contact between the at least one dye and oxygen in the air. A particularly suitable packaging mode can then be an aerosol device.

With the dyes according to the disclosure, it is also possible to produce bleaching agents in the absence of oxidation colorants and in the presence of an oxidizing agent in such conditions (for example hydrogen peroxide in an alkaline medium) that the oxidizing agent is able to bleach the keratin fibers by acting on the pigments initially present in the fibers.

The following non-limiting examples are illustrative of the invention.

EXAMPLE 1

The following dye composition was prepared:

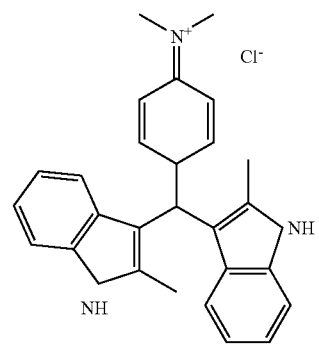

Compound 1

| | |
|---|---|
| {4-[Bis-(2-methyl-1H-indol-3-yl)-methylene]-cycolohexa-2,5-dienylidene}-dimethyl-ammonium chloride | 0.427 gm |
| Benzylic alcohol | 4.0 gm |
| Polyethyleneglycol 6OE | 6.0 gm |
| Hydroxyethylcellulose | 0.7 gm |
| Alkylpolyglucoside in aqueous solution at 60% MA* | 4.5 gm M.A. |
| Phosphate buffer qs | pH 7 |
| Deionised water qs | 100 gm |

*Active Matter

The above composition was applied on locks of natural or permanent-waved grey hair, with 90% white, and was left to act for 20 minutes. After rinsing with running water and drying, the hair was dyed in a shade of blue.

EXAMPLE 2

The following dye composition was prepared:

Compound 2

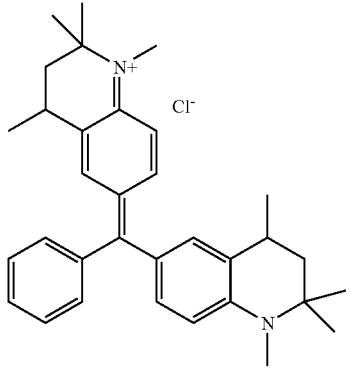

| | |
|---|---|
| 1,2,2,4-Tetramethyl-6-[phenyl-(1,2,2,4-tetramethyl-1,2,3,4,-tetrahydro-quinolin-6-yl)-methylene]-2,3,4,6-tetrahydroquinolinium chloride | 0.50 gm |
| Oleic diethanolamide | 3.0 gm |
| Lauric acid | 1.0 gm |
| Ethyleneglycol Monoethylether | 5.0 gm |
| Hydroxyethylcellulose | 2.0 gm |
| 2-amino-2-methyl-1-propanol qs | pH 9.5 |
| Demineralised water qs | 100 gm |

The above composition was applied on locks of natural or permanent-waved grey hair, with 90% white, and was left to act for 30 minutes. After rinsing with running water and drying, the hair was dyed in a shade of blue.

EXAMPLES 3 to 6

Four direct dyeing compounds were prepared and are shown in the following table:

(all contents expressed in grams)

| COMPOUND 1 | COMPOUND 2 |
|---|---|
| {4-[Bis-(2-methyl-1H-indol-3-yl)-methylene]-cyclohexa-2,5-dienylidene}-dimethyl-ammonium chlorure | 1,2,2,4-Tetramethyl-6-[phenyl-(1,2,2,4-tetramethyl-1,2,3,4-tetrahydro-quinolin-6-yl)-methylene]-2,3,4,6-tetrahydroquinolinium chloride |
| COMPOUND 3 | COMPOUND 4 |
| 1,2,2,3-Tetramethyl-5-[(1- | 9-Ethyl-3-[(9-ethyl- |

-continued

| methyl-2-phenyl-1H-indol-3-yl)-phenyl-methylene]-3,5-dihydro-2H-indolinum chloride | 9H-carbazol-3-yl)-phenyl-methylene]-3H-carbazolium chloride |
|---|---|

| | Example 3 | Example 4 | Example 5 | Example 6 |
|---|---|---|---|---|
| Direct dye of formula (1) | 0.2 | | | |
| Direct dye of formula (2) | | 0.2 | | |
| Direct dye of formula (3) | | | 0.2 | |
| Direct dye of formula (4) | | | | 0.2 |
| Crosslinked polyacrylic acid sold under the name Carbopol 2984 by Goodrich | 1.0 MA* | | | |
| Ammonium acrylate/acrylamide copolymer sold under the name Bozepol C Nouveau (New) by Hoechst | | 1.0 MA* | | |
| Crosslinked methacrylic acid/ethylacrylate copolymer sold in aqueous dispersion with 38% active matter under 538C by Coatex | | | 1.0 MA* | |
| Crosslinked acrylic acid/ethyl acrylate copolymer sold in aqueous dispersion with 28% active matter under the name Aculyn 33 by Rohm & Haas | | | | 1.0 MA* |
| Ethanol | 10 | 10 | 10 | 10 |
| 2-amino-2-methyl-1-propanol ams | pH9 | pH9 | pH9 | pH9 |
| Deionised water qs | 100 | 100 | 100 | 100 |

MA* Active Matter

The above compositions were each applied for 30 minutes on locks of natural grey hair with 90% white. The locks of hair were then rinsed, washed with a normal shampoo, and then dried.

The locks were then tinted in the following shades:

| Examples | Obtained shades |
|---|---|
| 3 | Powerful blue |
| 4 | Powerful blue |
| 5 | Powerful violet-blue |
| 6 | Powerful green |

EXAMPLES 7 TO 10

The following compositions 7(A) to 10(A) were prepared according to the invention, (contents grams):

| | COMPOSITION | | | |
|---|---|---|---|---|
| | 7 (A) | 8 (A) | 9 (A) | 10 (A) |
| Paratoluylenediamine | 0.25 | — | — | — |
| Para-aminophenol | 0.30 | 0.50 | 0.15 | — |
| Paraphenylenediamine | — | 0.20 | — | 0.30 |
| 5-N-(β-hydroxyethyl) amino 2-methyl phenol | 0.5 | 0.8 | 0.17 | — |
| 5-amino 2-methyl phenol | — | — | — | 0.30 |
| Colorant of structure (2) | 0.15 | — | — | — |
| Colorant of structure (3) | — | 0.20 | 0.05 | — |
| Colorant of structure (4) | — | — | — | 0.1 |
| Common dye support (*) | (*) | (*) | (*) | (*) |
| Water qs | 100 gm | 100 gm | 100 gm | 100 gm |

The common dye support used in the compositions 7(A) to 10(A) comprised the following:

| | |
|---|---|
| Polyglycerolated oleic alcohol with 2 moles of glycerol | 4.0 gm |
| Polyglycerolated oleic acid with 4 moles of glycerol, 78% of active matter (M.A.) | 5.69 gm M.A. |
| Oleic acid | 3.0 gm |
| Oleic amine with 2 moles of ethylene oxide sold under the trade name ETHOMEEN O12 by AKZO | 7.0 gm |
| Diethylaminopropyl laurylamino succinamate, sodium salt, with 55% M.A. | 3.0 gm M.A. |
| Oleic alcohol | 5.0 gm |
| Oleic acid diethanolamide | 12.0 gm |
| Propyleneglycol | 3.5 gm |
| Ethyl alcohol | 7.0 gm |
| Dipropyleneglycol | 0.5 gm |
| Propyleneglycol monomethylether | 9.0 gm |
| Sodium metabisulphite in aqueous solution, with 35% M.A. | 0.455 gm M.A. |
| Ammonium acetate | 0.8 gm |
| Antioxidant, sequestering agent | qs |
| Fragrance, preserving agent | qs |
| Ammonia with 20% of $NH_3$ | 10.0 gm |

At the moment of use, each of the compositions 7(A) to 10(A) was mixed with an equal quantity of a composition (B) comprising a solution of hydrogen peroxide at 20 volumes (6% by weight).

Each resulting composition (composition ready for use according to the invention) was applied for 30 minutes on locks of natural grey hair with 90% white. The locks of hair were then rinsed, washed with a normal shampoo and then dried.

The locks of hair were dyed in the shade mentioned in the following table:

| EXAMPLE (COMPOSITION) | OBTAINED SHADE |
|---|---|
| 7 [7(A)] | Deep blond with blue glints |
| 8 [8(A)] | Blond with violet-blue glints |
| 9 [9(A)] | Light blond with violet-blue glints |
| 10 [10(A)] | Blond with green glints |

The obtained shades showed very high tenacity towards subsequent shampoos.

According to a variant of the invention, the direct dyes may be incorporated in the dye compositions at the moment of use.

EXAMPLE 11

The following composition 11(A) was prepared:

| 1,4-diamino benzene | 0.40 gm |
| 5-amino 2-methyl phenol | 0.45 gm |
| Common dye support as described above for examples 7 to 10 | (*) |
| Deionised water qs | 100 gm |

The following composition 11(A') was prepared:

compound 5

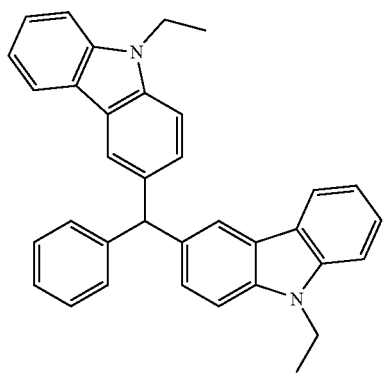

bis(9-ethyl-9H-carbazol-3-yl) phenylmethane

| Colorant of structure (5) | 4 gm |
| Quaternary polyammonium sold under the trade name CELQUAT SC-240 by National Starch | 10 gm |
| Sawdust qs | 100 gm |

At the moment of use, one part by weight of the composition 11(A) above was mixed with a 0.1 part by weight of the composition 11(A') and with one part by weight of a composition (B) comprising a solution of hydrogen peroxide at 20 volumes (6% by weight).

The resulting composition was applied for 30 minutes on locks of natural grey hair with 90% white. The hair was then rinsed with water, washed with a normal shampoo and then dried.

The hair was dyed with a light brown shade with glints of green, and was shown to be very resistant towards subsequent shampooing.

What is claimed is:

1. A composition for dyeing human keratin fibers comprising:
   a cosmetic medium suitable for dyeing human keratin fibers, wherein said medium is water or a mixture of water and at least one organic solvent suitable for dyeing human keratin fibers, and
   at least one dye, comprised in said medium and chosen from formulae (I), (Ibis), (Iter), (II), and (IIbis), their tautomeric forms, and their addition salts:

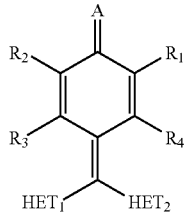
(I)

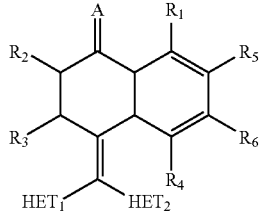
(Ibis)

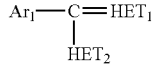
(Iter)

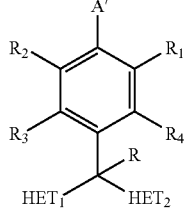
(II)

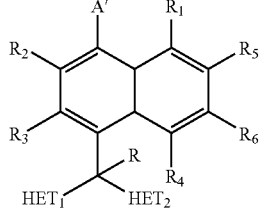
(IIbis)

in which:
   A is chosen from O, NH, N-alkyl N-hydroxyalkyl; ammonium; N-alkylammonium; N-(hydroxyalkyl) ammonium; N,N-dialkylammonium, N,N-di(hydroxyalkyl) ammonium, and N-(hydroxyalkyl) N-(alkyl) ammonium, in which the two alkyl groups may form, together with the nitrogen atom to which they are linked, a cycle that may be interrupted by at least one atom chosen from nitrogen, oxygen, and sulphur;
   $Ar_1$ is chosen from aryl, optionally substituted with at least one group Z,
   $HET_1$, $HET_2$, which may be the same or different, are chosen from heterocycle, optionally substituted with at least one group Z';

R₁ to R₆ and Z, Z', which may be the same or different, are chosen from hydrogen, halogen, —NHSO₃H; hydroxyl; alkyl; alkoxy; alkylthio; amino; monoalkylamino; and dialkylamino, in which the two alkyl groups may form, together with the nitrogen atom to which they are linked, a cycle that may be interrupted by at least one atom chosen from nitrogen, oxygen, and sulphur; heterocycle, nitro; aryl; acyl; alkoxycarbonyl; carboxamido; cyano; —CO₂H; —SO₃H; —PO₃H₂; and —PO₄H₂;

A' is chosen from hydrogen, hydroxyl, amino, (hydroxyalkyl)amino, di(hydroxyalkyl)amino, (hydroxyalkyl)(alkyl)amino, monoalkylamino, and dialkylamino, in which the two alkyl groups may form, together with the nitrogen atom to which they are linked, a cycle that may to be interrupted by at least one atom chosen from nitrogen, oxygen, and sulphur;

R is chosen from hydrogen, halogen; hydroxyl; alkoxy; and alkylthio.

2. A composition according to claim 1, wherein said aryl in Ar₁ is chosen from phenyl and naphthyl, and wherein for R₁ to R₆ and Z, Z', the halogen are chosen from F, Cl, Br and I.

3. A composition according to claim 1, wherein HET₁ and HET₂ are chosen from unsaturated heterocycle optionally substituted with at least one Z'.

4. A composition according to claim 3, wherein the unsaturated heterocycle are chosen from aromatic unsaturated heterocycle optionally substituted with at least one Z'.

5. A composition according to claim 1, wherein the heterocycle are chosen from thiophene, benzothiophene, furane, benzofurane, indole, indoline, carbazole, pyridine, dehydroquinoline, chromone, julolidine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

6. A composition according to claim 1, wherein HET₁, and HET₂ are chosen from thiophene, benzothiophene, furane, benzofurane, indole, indoline, carbazole, pyridine, dehydroquinoline, chromone, julolidine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

7. A composition for dyeing keratin fibers comprising, in a cosmetic medium suitable for dyeing, at least one dye chosen from the following compounds for which the counter-ions are specified or not, and their addition salts:

4-[Bis-(2-methyl-1H-indol-3-yl)-methylene]-cyclohexa-2,5-dienylidene}-dimethyl-ammonium;

1,2,2,4-Tetramethyl-6-[-phenyl-(1,2,2,4-tetramethyl-1,2,3,4-tetrahydro-quinolin-6-yl)-methylene]-2,3,4,6-tetrahydroquinolinium chloride;

1,2,2,3-Tetramethyl-5-[(1-methyl-2-phenyl-1H-indol-3-yl)-phenyl-methylene]-3,5-dihydro-2H-indolinium chloride;

9-Ethyl-3-[(9-ethyl-9H-carbazol-3-yl)-phenyl-methylene]-3H-carbazolium chloride;

1-Ethyl-3-[(1-ethyl-2-methyl-1H-indol-3-yl)-p-tolyl-methylene]-2-methyl-3a,7a-dihydro-3H-indolium;

6-{(4-Nitro-phenyl)-[1-(4-sulfo-butyl)-1,2,3,4-tetrahydro-quinolin-6-yl]-methylen}-1-(4-sulfo-butyl)-2,3,4,6-tetrahydro-quinolinium;

6-{(4–Cyano-phenyl)-[1-(4-sulfo-butyl)-1,2,3,4-tetrahydro-quinolin-6-yl]-methylen}-1-(4-sulfo-butyl)-2,3,4,6-tetrahydro-quinolinium;

Diethyl-{4-[(2-methyl-1H-indol-3-yl)-thiophen-2-yl-methylene]-cyclohexa-2,5-dienylidene}-ammonium;

1-Ethyl-3-[(1-éthyl-2-methyl-1H-indol-3-yl)-(4-methoxy-phenyl)-methylene]-2-methyl-3a,7a-dihydro-3H-indolium;

Ethanaminium, N-[4-[(3-carboxypyrazinyl)(1-ethyl-2-methyl-1H-indol-3-yl)methylene]-3-ethoxy-2,5-cyclohexadien-1-ylidene]-N-ethyl-, internal salt;

Ethanaminium, N-[4-[(3-carboxypyrazinyl)(1-ethyl-2-methyl-1H-indol-3-yl)methylene]-3-ethoxy-2,5-cyclohexadien-1-ylidene]-N-ethyl-, chloride;

Cyclohepta[b]furylium, 3-[[4-(dimethylamino)phenyl](2-oxo-2H-cyclohepta[b]furan-3-yl)methylene]-2,3-dihydro-2-oxo;

Methanaminium, N-[4-[bis(1,2,3,4,10,14b-hexahydro-2-methyldibenz[c,f]pyrazino[1,2-a]azepin-8-yl)methylene]-2,5-cyclohexadien-1-ylidene]-N-methyl-, perchlorate, diperchlorate;

Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-, perchlorate;

Methanaminium, N-[4-[bis(1,2,3,4,10,14b-hexahydro-2-methyldibenzo[c,f]pyrazino[1,2-a]azepin-8-yl)methylene]-2,5-cyclohexadien-1-ylidene]-N-methyl-;

Methanaminium, N-[4-[bis(2,3-dihydro-1,5-dimethyl-3-oxo-2-phenyl-1H-pyrazol-4-yl)methylene]-2,5-cyclohexadièn-1-ylidene]-N-methyl-;

Morpholinium, 4-[5-[[4-(dimethylamino)phenyl][5-(4-morpholinyl)-2-thienyl]methylene]-2(5H)-thienylidene]-, perchlorate;

Morpholinium, 4-[5-[[4-(dimethylamino)phenyl][5-(4-morpholinyl)-2-thienyl]methylene]-2(5H)-thienylidene]-;

1H-Indolizinium, 7-(dimethylamino)-1-[[7-(dimethylamino)-3-(ethoxycarbonyl)-1-indolizinyl][4-(dimethylamino)phenyl]methylene]-3-(ethoxycarbonyl)-, perchlorate;

1H-Indolizinium, 7-(dimethylamino)-1-[[7-(dimethylamino)-3-(ethoxycarbonyl)-1-indolizinyl][4-(dimethylamino)phenyl]methylene]-3-(ethoxycarbonyl)-;

Cyclohepta[b]pyrrolium, 3-[(1,2-dihydro-2-oxo-1-phenylcyclohepta[b]pyrrol-3-yl)[4-(dimethylamino)phenyl]methylene]-2,3-dihydro-2-oxo-1-phenyl-, hexafluorophosphate;

Cyclohepta[b]pyrrolium, 3-[(1,2-dihydro-2-oxo-1-phenylcyclohepta[b]pyrrol-3-yl)[4-(dimethylamino)phenyl]methylene]-2,3-dihydro-2-oxo-1-phenyl-;

Quinolinium, 6-[[4-(dimethylamino)phenyl](1,2,3,4-tetrahydro-1,2,2,4-tetramethyl-6-quinolinyl)methylene]-2,3,4,6-tetrahydro-1,2,2,4-tetraméthyl-, chloride;

Quinolinium, 6-[(1,2-dihydro-1,2,2,4-tetraméthyl-6-quinolinyl)[4-(dimethylamino)phenyl]methylene]-2,6-dihydro-1,2,2,4-tetramethyl-,chloride;

3H-Carbazolium, 9-ethyl-3-[(9-ethyl-9H-carbazol-3-yl)[4-(methylphenylamino)phenyl]methylene]-, tetrafluoroborate(1-);

3H-Carbazolium, 3-[[4-(dimethylamino)phenyl](9-ethyl-9H-carbazol-3-yl)methylene]-9-ethyl-, tetrafluoroborate(1-);

3H-Carbazolium, 9-ethyl-3-[(9-ethyl-9H-carbazol-3-yl)[4-(methylphenylamino)phenyl]methylene]-, perchlorate;

3H-Carbazolium, 9-ethyl-3-[(9-ethyl-9H-carbazol-3-yl)[4-(methylphenylamino)phenyl]methylene]-, bromide;

3H-Carbazolium, 9-ethyl-3-[(9-ethyl-9H-carbazol-3-yl)[4-(methylphenylamino)phenyl]methylene]-, chloride;

3H-Carbazolium, 3-[[4-(dimethylamino)phenyl](9-ethyl-9H-carbazol-3-yl)methylene]-9-ethyl-, bromide;

3H-Carbazolium, 3-[[4-(dimethylamino)phenyl](9-ethyl-9H-carbazol-3-yl)methylene]-9-ethyl-, chloride;

3H-Carbazolium, 9-ethyl-3-[(9-ethyl-9H-carbazol-3-yl)[4-(methylphenylamino)phenyl]methylene]-, iodide;

3H-Carbazolium, 3-[[4-(dimethylamino)phenyl](9-ethyl-9H-carbazol-3-yl)methylene]-9-ethyl-, iodide 3H-Carbazolium, 3-[[4-(dimethylamino)phenyl](9-ethyl-9H-carbazol-3-yl)methylene]-9-éthyl-, perchlorate;

1H-Pyrazolium, 4-[(2,3-dihydro-1,5-dimethyl-3-oxo-2-phenyl-1H-pyrazol-4-yl)[4-(trimethylammonio)phenyl]methylene]-4,5-dihydro-2,3-dimethyl-5-oxo-1-phenyl-, diperchlorate;

1H-Pyrazolium, 4-[(2,3-dihydro-1,5-dimethyl-3-oxo-2-phenyl-1H-pyrazol-4-yl)[4-(trimethylammonio)phenyl]methylene]-4,5-dihydro-2,3-dimethyl-5-oxo-1-phenyl- 5H-Benzo[a]carbazolium, 11-ethyl-5-[(11-ethyl-3-methoxy-8-methyl-11H-benzo[a]carbazol-5-yl)(4-nitrophenyl)methylene]-3-methoxy-8-methyl-, tetrafluoroborate;

5H-Benzo[a]carbazolium, 11-ethyl-5-[(11-ethyl-3-methoxy-8-methyl-11H-benzo[a]carbazol-5-yl)(4-nitrophenyl)methylene]-3-methoxy-8-methyl-;

5H-Benzo[a]carbazolium, 11-ethyl-5-[(11-ethyl-2-methoxy-8-methyl-11H-benzo[a]carbazol-5-yl)(4-nitrophenyl)methylene]-2-methoxy-8-methyl-, tetrafluoroborate;

5H-Benzo[a]carbazolium, 11-ethyl-5-[(11-ethyl-2-methoxy-8-methyl-11H-benzo[a]carbazol-5-yl)(4-nitrophenyl)methylene]-2-methoxy-8-methyl-;

5H-Benzo[a]carbazolium, 11-ethyl-5-[(11-ethyl-8-methoxy-11H-benzo[a]carbazol-5-yl)(4-nitrophenyl)methylene]-8-methoxy-, tetrafluoroborate;

5H-Benzo[a]carbazolium, 11-ethyl-5-[(11-ethyl-8-methoxy-11H-benzo[a]carbazol-5-yl)(4-nitrophenyl)methylene]-8-methoxy-;

5H-Benzo[a]carbazolium, 11-ethyl-5-[(11-ethyl-4-methoxy-11H-benzo[a]carbazol-5-yl)(4-nitrophenyl)methylene]-4-methoxy-, tetrafluoroborate;

5H-Benzo[a]carbazolium, 11-ethyl-5-[(11-ethyl-4-methoxy-11H-benzo[a]carbazol-5-yl)(4-nitrophenyl)methylene]-4-methoxy-;

5H-Benzo[a]carbazolium, 11-ethyl-5-[(11-ethyl-3-methoxy-11H-benzo[a]carbazol-5-yl)(4-nitrophenyl)methylene]-3-methoxy-, tetrafluoroborate;

5H-Benzo[a]carbazolium, 11-ethyl-5-[(11-ethyl-3-methoxy-11H-benzo[a]carbazol-5-yl)(4-nitrophenyl)methylene]-3-methoxy-;

5H-Benzo[a]carbazolium, 11-ethyl-5-[(11-ethyl-2-methoxy-11H-benzo[a]carbazol-5-yl)(4-nitrophenyl)methylene]-2-methoxy-, tetrafluoroborate;

5H-Benzo[a]carbazolium, 11-ethyl-5-[(11-ethyl-2-methoxy-11H-benzo[a]carbazol-5-yl)(4-nitrophenyl)methylene]-2-methoxy-;

5H-Benzo[a]carbazolium, 5-[(2-chloro-4-nitrophenyl)(11-ethyl-11H-benzo[a]carbazol-5-yl)methylene]-11-ethyl-, salt with trifluoromethanesulfonic acid (1:1);

5H-Benzo[a]carbazolium, 5-[(2-chloro-4-nitrophenyl)(11-ethyl-11H-benzo[a]carbazol-5-yl)methylene]-11-ethyl;

5H-Benzo[a]carbazolium, 11-ethyl-5-[(11-ethyl-11H-benzo[a]carbazol-5-yl)(4-nitrophenyl)methylene]-, tetrafluoroborate;

5H-Benzo[a]carbazolium, 11-ethyl-5-[(11-ethyl-11H-benzo[a]carbazol-5-yl)(4-nitrophenyl)methylene]-;

5H-Benzo[a]carbazolium, 5-[[4-(diethylamino)phenyl](11-ethyl-11H-benzo[a]carbazol-5-yl)methylene]-11-ethyl-, tetrafluoroborate(1-);

5H-Benzo[a]carbazolium, 5-[[4-(diethylamino)phenyl](11-ethyl-11H-benzo[a]carbazol-5-yl)methylene]-11-ethyl-;

5H-Benzo[a]carbazolium, 5-[[4-(dimethylamino)phenyl](11-ethyl-11H-benzo[a]carbazol-5-yl)methylene]-11-ethyl-, tetrafluoroborate(1-);

5H-Benzo[a]carbazolium, 5-[[4-(dimethylamino)phenyl](11-ethyl-11H-benzo[a]carbazol-5-yl)methylene]-11-ethyl-;

Salt of 1H-Pyrazolium, 4-[(2,3-dihydro-1,5-dimethyl-3-oxo-2-phenyl-1H-pyrazol-4-yl)[4-(dimethylamino)phenyl]methylene]-4,5-dihydro-2,3-dimethyl-5-oxo-1-phenyl- and a monoacid;

3H-Carbazolium, 3-[[4-[bis(phenylmethyl)amino]phenyl](9-ethyl-9H-carbazol-3-yl)methylène]-9-ethyl-, iodide;

3H-Imidazo[1,2-a]benzimidazolium, 3-[[4-(dimethylamino)phenyl](9-methyl-2-phenyl-9H-imidazo[1,2-a]benzimidazol-3-yl)methylene]-9-methyl-2-phenyl-, chloride;

3H-Imidazo[1,2-a]benzimidazolium, 3-[[4-(dimethylamino)phenyl](2,9-dimethyl-9H-imidazo[1,2-a]benzimidazol-3-yl)methylene]-2,9-dimethyl-, bromide;

1H-Pyrazolium, 4-[(2,3-dihydro-1,5-dimethyl-3-oxo-2-phenyl-1H-pyrazol-4-yl)[4-(dipropylamino)phenyl]methylene]-4,5-dihydro-2,3-dimethyl-5-oxo-1-phenyl-;

1H-Pyrazolium, 4-[[4-(diethylamino)phenyl](2,3-dihydro-1,5-dimethyl-3-oxo-2-phenyl-1H-pyrazol-4-yl)methylene]-4,5-dihydro-2,3-dimethyl-5-oxo-1-phenyl-;

1H-Pyrazolium, 4-[(2,3-dihydro-1,5-dimethyl-3-oxo-2-phenyl-1H-pyrazol-4-yl)(4-nitrophenyl)methylene]-4,5-dihydro-2,3-dimethyl-5-oxo-1-phenyl-;

1H-Pyrazolium, 4-[(2,3-dihydro-1,5-dimethyl-3-oxo-2-phenyl-1H-pyrazol-4-yl)[4-(dimethylamino)phenyl]methylene]-4,5-dihydro-2,3-dimethyl-5-oxo-1-phenyl-;

1H-Pyrazolium, 4-[(4-aminophenyl)(2,3-dihydro-1,5-dimethyl-3-oxo-2-phenyl-1H-pyrazol-4-yl)methylene]-2,3-dimethyl-5-oxo-1-phenyl;

3H-Indolizinium, 3-[[4-(dimethylamino)phenyl](6-ethenyl-1,2-dimethyl-3-indolizinyl)methylene]-6-ethenyl-1,2-dimethyl-;

3H-Indolizinium, 3-[p-(dimethylamino)-α-(6-ethyl-1,2-dimethyl-3-indolizinyl)benzylidene]-6-ethyl-1,2-dimethyl-, iodide;

3H-Indolizinium, 3-[p-(dimethylamino)-α-(1,2-dimethyl-6-vinyl-3-indolizinyl)benzylidene]-1,2-dimethyl-6-vinyl-, perchlorate;

2-Pyrazolinium, 4-(p-amino-α-antipyrinylbenzylidene)-2,3-dimethyl-5-oxo-1-phenyl-, perchlorate;

2-Pyrazolinium, 4-(α-antipyrinyl-p-nitrobenzylidene)-2,3-dimethyl-5-oxo-1-phenyl-, perchlorate;

2-Pyrazolinium, 4-[α-antipyrinyl-p-(diethylamino)benzylidene]-2,3-dimethyl-5-oxo-1-phenyl-, perchlorate;

2-Pyrazolinium, 4-[α-antipyrinyl-p-(dimethylamino)benzylidene]-2,3-dimethyl-5-oxo-1-phenyl-, perchlorate;
Methylium, bis[6-(dimethylamino)-3-methyl-1H-indol-2-yl][4-(dimethylamino)phenyl], perchlorate;
Methylium, bis[6-(dimethylamino)-3-methyl-1H-indol-2-yl][4-(dimethylamino)phenyl]-;
Methylium, bis[6-(dimethylamino)-3-methyl-1H-indol-2-yl](4-nitrophenyl)-, perchlorate;
Methylium, bis[6-(dimethylamino)-3-methyl-1H-indol-2-yl](4-nitrophenyl)-;
Methylium, bis(benzo[b]thien-2-yl)[4-(dimethylamino)phenyl]-, tetrafluoroborate;
Methylium, bis(benzo[b]thien-2-yl)[4-(dimethylamino)phenyl]-;
Methylium, [4-(dimethylamino)phenyl]bis(1-methyl-1H-pyrrol-2-yl)-, tetrafluoroborate;
Methylium, [4-(dimethylamino)phenyl]bis(1-methyl-1H-pyrrol-2-yl)-;
Diantipyrinyl(p-nitrophenyl)methylium perchlorate;
Methylium, bis(9,10-dihydro-9,9,10-trimethyl-3-acridinyl)[4-(dimethylamino)phenyl]-, chloride;
Methylium, [4-(dimethylamino)phenyl]bis(10-methyl-10H-phenothiazin-2-yl)-, chloride;
3H-Pyrazol-3-one, 4,4'-[[4-(dimethylamino)phenyl]methylene]bis[1,2-dihydro-1,5-dimethyl-2-phenyl-, mono[tetrafluoroborate(1-)];
3H-Pyrazol-3-one, 4,4'-[[4-(dimethylamino)phenyl]methylene]bis[1,2-dihydro-1,5-dimethyl-2-phenyl-, bis[tetrafluoroborate(1-)];
Salt of 3H-Pyrazol-3-one, 4,4'-[[4-(dimethylamino)phenyl]methylene]bis[1,2-dihydro-1,5-dimethyl-2-phenyl- and a diacid;
Salt of 3H-Pyrazol-3-one, 4,4'-[[4-(dimethylamino)phenyl]methylene]bis[1,2-dihydro-1,5-dimethyl-2-phenyl-, and a monoacid;
Quinolinium, 4,4'-[(4-nitrophenyl)methylene]bis[1-ethyl-, dichloride;
Methylium, bis(9-ethyl-9H-carbazol-3-yl)(4-nitrophenyl)-, iodide;
Methylium, [4-(dimethylamino)phenyl]bis(9-ethyl-9H-carbazol-3-yl)-, iodide;
Methylium, 9H-carbazol-3-yl[4-(dimethylamino)phenyl](6-methyl-9H-carbazol-3-yl)-;
Quinolizinium, 2,2'-[(4-nitrophenyl)methylene]bis[1,2,3,4-tetrahydro-1-oxo-;
Methylium, 9H-carbazol-3-yl[4-(dimethylamino)phenyl](6-methyl-9H-carbazol-3-yl)-, tetrafluoroborate;
Borate(1-), tetrafluoro-, 9H-carbazol-3-yl[4-(dimethylamino)phenyl](6-methyl-9H-carbazol-3-yl)methylium;
6-Methyl-3,3'-dicarbazolyl-p-dimethylaminophenylmethyl fluoroborate;
6,6'-Dichloro-9,9'-dibutyl-3,3'-dicarbazolyl-p-nitrophenylmethyl chlorure;
Quinolizinium, 2,2'-(p-nitrobenzylidene)bis[1,2,3,4-tetrahydro-1-oxo-, dipicrate;
Picric acid salt of 2,2'-(p-nitrobenzylidene)bis[1,2,3,4-tetrahydro-1-oxoquinolizinium];
Quinolizinium, 2,2'-(p-nitrobenzylidene)bis[1,2,3,4-tétrahydro-1-oxo-, diperchlorate;
Benzylium, p-(diethylamino)-α,α-bis(2,3-dimethyl-5-oxo-1-phenyl-3-pyrazolin-4-yl)-;
Benzylium, α,α-diantipyrinyl-p-(dimethylamino)-;
Benzylium, α,α-bis(2,3-dimethyl-5-oxo-1-phenyl-3-pyrazolin-4-yl)-p-nitro-; and
Benzylium, p-amino-α,α-di-4-antipyrinyl-.

8. A composition according to claim 1, wherein the at least one dye is present in an amount ranging from about 0.0001 to about 10% by weight of the total weight of the dye composition.

9. A composition according to claim 8, wherein the at least one dye is present in an amount ranging from about 0.005 to about 10% by weight of the total weight of the dye composition.

10. A composition according to claim 9, wherein the at least one dye is present in an amount ranging from about 0.01 to about 6% by weight of the total weight of the dye composition.

11. A composition according to claim 1, further comprising at least one direct dye different from said at least one dye chosen from formulae (I), (Ibis), (Iter), (II), and (IIbis), their tautomeric forms, and their addition salts.

12. A composition according to claim 11, wherein said at least one direct dye different from said at least one dye chosen from formulae (I), (Ibis), (Iter), (II), and (IIbis), their tautomeric forms, and their addition salts, is chosen from neutral, acid, and cationic benzenic nitrated direct dyes, neutral, acid, and cationic azoic direct dyes, quinonic direct dyes, azinic direct dyes, triarylmethanic direct dyes, indoaminic direct dyes, and natural direct dyes.

13. A composition according to claim 12, wherein said quinonic direct dyes are chosen from neutral, acid, and cationic anthraquinonic direct dyes.

14. A composition according to claim 11, wherein said at least one direct dye different from said at least one dye chosen from formulae (I), (Ibis), (Iter), (II), and (IIbis), their tautomeric forms, and their addition salts, is present in an amount ranging from about 0.001 to about 20% by weight of the total weight of the dye composition.

15. A composition according to claim 1, further comprising at least one oxidation base and optionally further comprising at least one coupler.

16. A composition according to claim 15, wherein said at least one oxidation base is chosen from paraphenylenediamines, bis-phenylalkylenediamines, para-aminophenols, ortho-aminophenols, heterocyclic bases, and their addition salts.

17. A composition according to claim 1, further comprising at least one coupler chosen from metaphenylenediamine couplers, meta-aminophenol couplers, metadiphenol couplers, naphthalenic couplers, heterocyclic couplers, and their addition salts.

18. A composition according to claim 15, wherein said at least one oxidation base and said optional at least one coupler is each present in an amount ranging from about 0.001 to about 10% by weight, by weight of the total weight of the dye composition.

19. A composition according to claim 15, wherein said at least one oxidation base and said optional at least one coupler is each present in an amount ranging from about 0.005 to about 6% by weight, by weight of the total weight of the dye composition.

20. A composition according to claim 1, having a pH ranging from about 3 to about 12.

21. A composition according to claim 20, having a pH ranging from about 5 to about 11.

22. A composition according to claim 21 having a pH ranging from about 6 to about 8.5.

23. A method for the direct dyeing of keratin fibers comprising:
applying on said keratin fibers at least one composition for dyeing keratin fibers comprising, in a cosmetic medium suitable for dyeing, at least one dye chosen from formulae (I), (Ibis), (Iter), (II), and (IIbis), their tautomeric forms, and their addition salts:

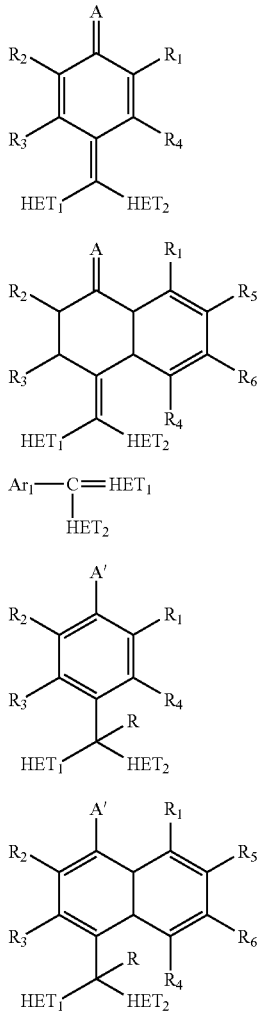

in which:

A is chosen from O, NH, N-alkyl N-hydroxyalkyl; ammonium; N-alkylammonium; N-(hydroxyalkyl) ammonium; N,N-dialkylammonium, N,N-di(hydroxyalkyl) ammonium, and N-(hydroxyalkyl) N-(alkyl) ammonium, in which the two alkyl groups may form, together with the nitrogen atom to which they are linked, a cycle that may be interrupted by at least one atom chosen from nitrogen, oxygen, and sulphur;

$Ar_1$ is chosen from aryl, optionally substituted with at least one group Z, $HET_1$, $HET_2$, which may be the same or different, are chosen from heterocycle, optionally substituted with at least one group Z';

$R_1$ to $R_6$ and Z, Z', which may be the same or different, are chosen from hydrogen, halogen, —$NHSO_3H$; hydroxyl; alkyl; alkoxy; alkylthio; amino; monoalkylamino; and dialkylamino, in which the two alkyl groups may form, together with the nitrogen atom to which they are linked, a cycle that may be interrupted by at least one atom chosen from nitrogen, oxygen, and sulphur; heterocycle, nitro; aryl; acyl; alkoxycarbonyl; carboxamido; cyano; —$CO_2H$; —$SO_3H$; —$PO_3H_2$; and —$PO_4H_2$;

A' is chosen from hydrogen, hydroxyl, amino, (hydroxyalkyl)amino, di(hydroxyalkyl)amino, (hydroxyalkyl)(alkyl)amino, monoalkylamino, and dialkylamino, in which the two alkyl groups may form, together with the nitrogen atom to which they are linked, a cycle that may to be interrupted by at least one atom chosen from nitrogen, oxygen, and sulphur;

R is chosen from hydrogen, halogen; hydroxyl; alkoxy; and alkylthio, observing a pause time, and rinsing said fibers.

24. A method according to claim 23, wherein said keratin fibers are human keratin fibers.

25. A method according to claim 24, wherein said human keratin fibers are hair.

26. A method according to claim 23, wherein the pause time observed ranges from about 3 to about 50 minutes.

27. A method according to claim 26, wherein the pause time observed ranges from about 5 to about 30 minutes.

28. A method for dyeing keratin fibers comprising
applying to said fibers at least one dye chosen from either formulae (II) and (IIbis), their tautomeric forms, and their addition salts, as recited in claim 1, or formulae (I), (Ibis), and (Iter), their tautomeric forms, and their addition salts, as recited in claim 1,
applying to said fibers at least one oxidation base and optionally at least one coupler, and
developing with at least one oxidizing agent the color at acid, neutral or alkaline pH.

29. A method according to claim 28, wherein said keratin fibers are human keratin fibers.

30. A method according to claim 29, wherein said human keratin fibers are hair.

31. A method according to claim 28, wherein said at least one oxidizing agent is chosen from hydrogen peroxide, carbamide peroxide, alkaline metal bromates, persalts, peracids, and oxidase enzymes.

32. A method according to claim 31, wherein said persalts are chosen from perborates and persulphates, and said oxidase enzymes are chosen from peroxydases, oxydoreductases with 2 electrons, and oxygenases with 4 electrons.

33. A method according to claim 32, wherein said oxydoreductases with 2 electrons are chosen from uricases and wherein said oxygenases with 4 electrons are chosen from laccases.

34. A device or kit with at least two separate compartments, comprising
a first compartment comprising a dyeing composition comprising at leat one dye chosen from either formulae (II) and (IIbis), their tautomeric forms, and their addition salts, as recited in claim 1, or formulae (I), (Ibis), and (Iter), their tautomeric forms, and their addition salts, as recited in claim 1, at least one oxidation base, and optionally at least one coupler, and
a second compartment comprising an oxidizing composition.

* * * * *

UNITED STATES PATENT AND TRADEMARK OFFICE
CERTIFICATE OF CORRECTION

PATENT NO. : 7,217,297 B2
APPLICATION NO. : 10/746501
DATED : May 15, 2007
INVENTOR(S) : Frédéric Guerin et al.

It is certified that error appears in the above-identified patent and that said Letters Patent is hereby corrected as shown below:

In claim 1, column 20, line 66, "heterocycle," should read --heterocycles,--.

In claim 1, column 21, line 16, "may to be interrupted" should read --may be interrupted--.

In claim 2, column 21, line 22, "halogen" should read --halogens--.

In claim 3, column 21, line 25, "heterocycle" should read --heterocycles--.

In claim 4, column 21, line 28, "heterocycle" should read --heterocycles--.

In claim 4, column 21, line 29, "heterocycle" should read --heterocycles--.

In claim 5, column 21, line 31, "heterocycle" should read --heterocycles--.

In claim 6, column 21, lines 39-40, "$HET_1$, and $HET_2$ are" should read --$HET_1$ and $HET_2$ are--.

In claim 7, column 21, lines 54-56,
"1,2,2,4-Tetramethyl-6-[-phenyl-(1,2,2,4-tetramethyl-1,2,3,4-tetrahydro-quinolin-6-yl)-methylene]-2,3,4,6-tetrahydroquinolinium chloride;"
should read
--1,2,2,4-Tetramethyl-6-[phenyl-(1,2,2,4-tetramethyl-1,2,3,4-tetrahydro-quinolin-6-yl)-methylene]-2,3,4,6-tetrahydroquinolinium chloride;--.

In claim 7, column 22, lines 6-8,
"1-Ethyl-3-[(1-éthyl-2-methyl-1H-indol-3-yl)-(4-methoxy-phenyl)-methylene]-2-methyl-3a,7a-dihydro-3H-indolium;"
should read
--1-Ethyl-3-[(1-ethyl-2-methyl-1H-indol-3-yl)-(4-methoxy-phenyl)-methylene]-2-methyl-3a,7a-dihydro-3H-indolium;--.

In claim 7, column 22, lines 29-31,
"Methanaminium, N-[4-bis(2,3-dihydro-1,5-dimethyl-3-oxo-2-phenyl-1H-pyrazol-4-yl)methylene]-2,5-cyclohexadièn-l-ylidene]-N-methyl-;"
should read
--Methanaminium, N-[4-bis(2,3-dihydro-1,5-dimethyl-3-oxo-2-phenyl-1H-pyrazol-4-yl)methylene]-2,5-cyclohexadien-l-ylidene]-N-methyl-;--.

UNITED STATES PATENT AND TRADEMARK OFFICE
CERTIFICATE OF CORRECTION

PATENT NO. : 7,217,297 B2
APPLICATION NO. : 10/746501
DATED : May 15, 2007
INVENTOR(S) : Frédéric Guerin et al.

It is certified that error appears in the above-identified patent and that said Letters Patent is hereby corrected as shown below:

In claim 7, column 22, lines 53-55,
"Quinolinium, 6-[[4-(dimethylamino)phenyl](1,2,3,4-tetrahydro-1,2,2,4-tetramethyl-6-quinolinyl)methylene]-2,3,4,6-tetrahydro-1,2,2,4-tetraméthyl-, chloride;"
should read
--Quinolinium, 6-[[4-(dimethylamino)phenyl](1,2,3,4-tetrahydro-1,2,2,4-tetramethyl-6-quinolinyl)methylene]-2,3,4,6-tetrahydro-1,2,2,4-tetramethyl-, chloride;--.

In claim 7, column 22, lines 56-58,
"Quinolinium, 6-[(1,2-dihydro-1,2,2,4-tetramethyl-6-quinolinyl)[4-(dimethylamino)phenyl]methylene)-2,6-dihydro-1,2,2,4-tetramethyl-, chloride;"
should read
--Quinolinium, 6-[(1,2-dihydro-1,2,2,4-tetraméthyl-6-quinolinyl)[4-(dimethylamino)phenyl]methylene)-2,6-dihydro-1,2,2,4-tetramethyl-, chloride;--.

In claim 7, column 23, lines 13-14,
"3H-Carbazolium, 3-[[4-(dimethylamino)phenyl](9-ethyl-9H-carbazol-3-yl)methylene]-9-éthyl-, perchlorate;"
should read
--3H-Carbazolium, 3-[[4-(dimethylamino)phenyl](9-ethyl-9H-carbazol-3-yl)methylene]-9-ethyl-, perchlorate;--.

In claim 7, column 23, lines 19-22,
"1H-Pyrazolium, 4-[(2,3-dihydro-1,5-dimethyl-3-oxo-2-phenyl-1H-pyrazol-4-yl)[4-(trimethylammonio)phenyl]methylene]-4,5-dihydro-2,3-dimethyl-5-oxo-l-phenyl-"
should read
--1H-Pyrazolium, 4-[(2,3-dihydro-1,5-dimethyl-3-oxo-2-phenyl-1H-pyrazol-4-yl)[4-(trimethylammonio)phenyl]methylene]-4,5-dihydro-2,3-dimethyl-5-oxo-1-phenyl-;--.

In claim 7, column 24, lines 23-25,
"3H-Carbazolium, 3-[[4-[bis(phenylmethyl)amino]phenyl](9-ethyl-9H-carbazol-3-yl)methylène]-9-ethyl-, iodide;"
should read
--3H-Carbazolium, 3-[[4-[bis(phenylmethyl)amino]phenyl](9-ethyl-9H-carbazol-3-yl)methylene]-9-ethyl-, iodide;--.

UNITED STATES PATENT AND TRADEMARK OFFICE
CERTIFICATE OF CORRECTION

PATENT NO. : 7,217,297 B2
APPLICATION NO. : 10/746501
DATED : May 15, 2007
INVENTOR(S) : Frédéric Guerin et al.

It is certified that error appears in the above-identified patent and that said Letters Patent is hereby corrected as shown below:

In claim 7, column 25, lines 54-55, "6,6'-Dichloro-9,9'-dibutyl-3,3'-dicarbazolyl-p-nitrophenylmethyl chlorure;"
should read
--6,6'-Dichloro-9,9'-dibutyl-3,3'-dicarbazolyl-p-nitrophenylmethyl chloride;--

In claim 7, column 25, lines 60-61,
"Quinolizinium, 2,2'-(p-nitrobenzylidene)bis[1,2,3,4-tétrahydro-1-oxo-, diperchlorate;"
should read
--Quinolizinium, 2,2'-(p-nitrobenzylidene)bis[1,2,3,4-tetrahydro-l-oxo-, diperchlorate;--.

In claim 18, column 26, line 50,
"10% by weight, by weight of the total weight" should read
--10% by weight of the total weight--.

In claim 19, column 26, line 55,
"6% by weight, by weight of the total weight" should read
--6% by weight of the total weight--.

In claim 23, column 28, line 11, "may to be interrupted" should read --may be interrupted--.

In claim 34, column 28, line 55, "at leat" should read --at least--.

Signed and Sealed this

Fourteenth Day of August, 2007

JON W. DUDAS
*Director of the United States Patent and Trademark Office*